(12) United States Patent
Dechelette et al.

(10) Patent No.: US 10,722,375 B2
(45) Date of Patent: Jul. 28, 2020

(54) SUBTALAR IMPLANT FOR ARTHROEREISIS OF THE TALOCALCANEAL JOINT

(71) Applicant: NEOSTEO, Nantes (FR)

(72) Inventors: Maxime Dechelette, Petit Mars (FR); Sylvain Sorin, Nantes (FR)

(73) Assignee: NEOSTEO, Nantes (FR)

( * ) Notice: Subject to any disclaimer, the term of this patent is extended or adjusted under 35 U.S.C. 154(b) by 62 days.

(21) Appl. No.: 16/043,687

(22) Filed: Jul. 24, 2018

(65) Prior Publication Data

US 2019/0029837 A1 Jan. 31, 2019

(30) Foreign Application Priority Data

Jul. 25, 2017 (FR) ..................... 17 57029

(51) Int. Cl.
*A61F 2/42* (2006.01)
*A61B 17/56* (2006.01)
(Continued)

(52) U.S. Cl.
CPC .......... *A61F 2/4202* (2013.01); *A61B 17/562* (2013.01); *A61F 2/4606* (2013.01);
(Continued)

(58) Field of Classification Search
CPC ...... A61F 2002/4223; A61F 2002/3078; A61F 2002/30143; A61F 2002/3092;
(Continued)

(56) References Cited

U.S. PATENT DOCUMENTS 5,769,899 A * 6/1998 Schwartz .............. A61L 27/227
606/77
6,074,423 A * 6/2000 Lawson .................. A61F 2/446
606/247

(Continued)

FOREIGN PATENT DOCUMENTS

| EP | 3061423 A2 | 8/2016 |
| WO | 2012100054 A1 | 7/2012 |
| WO | 2013123366 A1 | 8/2013 |

OTHER PUBLICATIONS

French Search Report dated Apr. 12, 2018 for corresponding French Application No. 1757029, filed Jul. 25, 2017.
(Continued)

*Primary Examiner* — Brian A Dukert
*Assistant Examiner* — Amanda M Barkan
(74) *Attorney, Agent, or Firm* — David D. Brush; Westman, Champlin & Koehler, P.A.

(57) ABSTRACT

A subtalar implant for arthroereisis of the talocalcaneal joint. The implant is intended to be inserted into the talocalcaneal joint via its lateral orifice and has an oblong shape that extends longitudinally along an axis of insertion of the implant. The implant includes: a head with the shape of a cone of revolution centred on the axis of insertion; an anchoring thread; and a rod having the shape of a cylinder of revolution. The rod has, on its surface, the anchoring thread and being configured to be inserted up to the axis of rotation of the talocalcaneal joint. The head has, on its radially outer surface, a retaining element for retaining the implant in rotation about the axis of insertion, the retaining element exerting retention against a colonising tissue.

12 Claims, 3 Drawing Sheets

(51) Int. Cl.
*A61F 2/46* (2006.01)
*A61F 2/30* (2006.01)

(52) U.S. Cl.
CPC ............... *A61F 2002/3085* (2013.01); *A61F 2002/30143* (2013.01); *A61F 2002/30212* (2013.01); *A61F 2002/30217* (2013.01); *A61F 2002/30232* (2013.01); *A61F 2002/30313* (2013.01); *A61F 2002/30322* (2013.01); *A61F 2002/30622* (2013.01); *A61F 2002/30754* (2013.01); *A61F 2002/30777* (2013.01); *A61F 2002/4207* (2013.01); *A61F 2002/4223* (2013.01); *A61F 2002/4619* (2013.01); *A61F 2002/4629* (2013.01)

(58) Field of Classification Search
CPC ...... A61F 2002/4217; A61F 2002/3085; A61F 2002/30138; A61F 2002/30146; A61F 2002/30149; A61F 2002/30154; A61F 2002/30156
See application file for complete search history.

(56) References Cited

U.S. PATENT DOCUMENTS

| | | | |
|---|---|---|---|
| 7,033,398 B2* | 4/2006 | Graham | A61B 17/562 606/304 |
| 8,092,547 B2 | 1/2012 | Lepow et al. | |
| 8,545,572 B2* | 10/2013 | Olson | A61B 17/8605 623/21.18 |
| 9,125,701 B2 | 9/2015 | Pech et al. | |
| 2005/0187636 A1 | 8/2005 | Graham | |
| 2009/0099664 A1 | 4/2009 | Forrester | |
| 2013/0304224 A1 | 11/2013 | Schmidt et al. | |

OTHER PUBLICATIONS

English translation of the Written Opinion for corresponding French Application No. 1757029, filed Jul. 25, 2017.

* cited by examiner

SUBTALAR IMPLANT FOR ARTHROEREISIS OF THE TALOCALCANEAL JOINT

CROSS-REFERENCE TO RELATED APPLICATIONS

This Application claims priority to and the benefit of FR1757029, filed in France on Jul. 25, 2017, the content of which is incorporated herein by reference in its entirety.

FIELD OF THE DISCLOSURE

The field of the disclosure is that of the design and the manufacturing of implantable medical devices for arthroereisis. More precisely, the disclosure relates to an extra-osseous implant, for arthroereisis of the talocalcaneal joint, the implant being intended to be inserted into the talocalcaneal joint via its lateral orifice.

BACKGROUND OF THE DISCLOSURE

Subtalar arthroereisis is a surgical operation practiced in the context of curing flexible flatfoot, in particular in children and adolescents.

Flatfoot syndrome is characterised by an instability of the talocalcaneal joint. This instability causes a phenomenon of hyperpronation during the placement of a load on the foot, which leads to a collapse of the plantar arch. The main clinical consequences are:
 pain;
 walking disorders;
 a rigidity of the Achilles tendon during walking;
 a deterioration of the peripheral joints due to a modification of the distribution of the loads.

Subtalar arthroereisis allows the movement of the joint to be limited by causing blocking via an implant.

For not very advanced stages of flatfoot, and in particular when the flatfoot is called "flexible", arthroereisis is an operation that combines a plurality of clinical benefits with respect to other therapeutic options.

Indeed, arthroereisis is a fast operation that requires a minimal incision and does not lead to the cutting of bone. Arthroereisis also allows a correction obtained to be preserved, even after the extraction of the implant used to carry out the correction. Thus, this is an operation that is reversible in the case of complications via simple removal of the implant as mentioned above.

In order to carry out the arthroereisis, the implant (generally an extra-osseous screw) is inserted into the sinus tarsi oriented in an anterolateral position towards a posterior-medial position. In other words, the implant is inserted into the talocalcaneal joint via its lateral orifice.

After the insertion, the implant must rest on the surface of the calcaneus in a "free float" configuration. After immobilisation, fibrous tissue, called colonising tissue, must colonise rough spots and cavities of the implant in such a way as to keep it in place in situ.

According to a current conventional design, the subtalar implants for arthroereisis of the talocalcaneal joint are in the form of a screw, that is to say, a generally conical oblong shape of revolution provided with a plurality of helical grooves. The helical grooves form a screw pitch that is not intended to move the implant forward by screwing it, but only act as a substrate for the fibrous regrowth of the colonising tissue. Indeed, the colonising tissue attaches in the helical grooves in order to produce a resistance to traction along the axis of insertion of the implant.

This conventional design of the implants has disadvantages, however.

Indeed, recurrent complications leading to the removal of the implant are noted in the literature.

A main complication lies in a backward movement of the implant, and potentially to the creation of a discomfort related to the backwards movement of the implant (inflammation of the sinus tarsi, synovitis, etc.).

The backwards movement of the implant is generally attributed to the shape of the implant. Indeed, during walking, a stress is applied to the generally conical contour of revolution of the implant. This stress takes the form of micromovements and leads to a phenomenon of unscrewing of the implant.

The stresses on the generally conical contour of revolution of the implant are indeed transformed into an axial movement of translation, which leads to the phenomenon of unscrewing because of the helical thread (helical groove or screw pitch).

In order to provide better anchoring for the tissue, a plurality of solutions have been proposed:
 the patent document published as U.S. Pat. No. 8,092,547 B2 proposes integrating holes around the periphery of the implant, these holes opening or not opening onto a cannula. The implant thus has a conical shape having an anchoring thread on the radially outer surface of the cone;
 the patent document published as US 2009/0099664 A1, proposes a conical implant having, on its radially outer surface, an anchoring thread, and integrating grooves inside the hollows formed by the anchoring thread;
 the patent documents published as U.S. Pat. No. 8,092,547 B2 and WO 2012/100054 A1 propose integrating profiles of threads qualified as negative, that is to say, producing an undercut.

The patent document published as WO 2012/100054 A1, cited above, also proposes an implant that does not have a conical portion and that has, instead of this conical portion, a spheroidal portion so as to provide uniform blocking of the joint during the presence of an anatomical particularity or of the implantation technique of the surgeon. Indeed, this document specifies that a conical implant can easily be implanted in such a way that it produces a pressure that is too low or too high on the talocalcaneal joint.

Finally, the prior art proposes the patent document published as U.S. Pat. No. 9,125,701 B2 that describes an implant manufactured using a plurality of components and that is based on the principle of the screw-expanding anchor. The implementation of such an implant is more complicated and costlier than a machined one-piece implant. Also, mechanical complications caused by the nature of the assembly may occur.

The patent document published as US 2013/0304224 A1 is also known, this document describing an implant comprising a main body and fastening elements independent of the main body. The fastening elements consist of screws to be inserted into the main body, these screws being designed to extend out of the main body in such a way as to be anchored in osseous structures. The implant described in this document is designed to carry out an arthrodesis, that is to say, that its goal is to lead to the creation of osseous fusion in a pathological joint. Such an implant is not suitable for carrying out an arthroereisis.

The goal of the solutions proposed by the prior art is to provide better anchoring for the colonising tissue, but these solutions can nevertheless contribute to the phenomenon of osseous irritation or even erosion. The implants presented by the prior art also constantly introduce a propensity to unscrewing that is not completely solved by the proposed solutions.

SUMMARY

An aspect of the present application relates to a subtalar implant for arthroereisis of the talocalcaneal joint, the implant intended to be inserted into the talocalcaneal joint via its lateral orifice and having an oblong shape that extends longitudinally along an axis of insertion of the implant, the implant being one-piece and comprising:

a head with the shape of a cone of revolution centred on the axis of insertion;

an anchoring thread;

characterised in that it comprises a rod having the shape of a cylinder of revolution centred on the axis of insertion, the rod having, on its surface, the anchoring thread and intended to be inserted up to the axis of rotation of the talocalcaneal joint, the head flaring out from the rod and being located upstream of the head along the axis of insertion of the implant, the head having, on its radially outer surface, retaining elements for retaining the implant in rotation about the axis of insertion, the retaining elements being intended to exert retention against a colonising tissue, depressions with respect to the shape of a cone of revolution of the head;

at least one recess located inside the depressions, the recess(es) communicating with each other inside the head in order to create at least one annular cavity intended to be colonised by colonising tissue, and in that, in a transverse cross-section perpendicular to the axis of insertion:

the head is inscribed inside a polygon (P), the sides of which extend at the depressions;

the annular cavity or cavities have a polygonal shape suitable for allowing the inscription of a fibrous integration polygon inside the head.

Such a subtalar implant for arthroereisis of the talocalcaneal joint does not have a or has little propensity to be unscrewed under the action of micromovements caused by the walking cycle.

Indeed, due to the positioning of the anchoring thread on the surface of the rod, and the insertion of the rod up to the axis of rotation of the talocalcaneal joint, the movements at the axis of the joint are zero or at the very least greatly reduced near this anchoring thread. This has the effect that the implant has an almost zero risk of undesired unscrewing related to the presence of this anchoring thread.

Also, the head of the implant has the shape of a cone of revolution centred on the axis of insertion. This head allows homogenous and progressive penetration of the implant during its positioning along the axis of insertion via the lateral orifice of the talocalcaneal joint. The shape of the head allows precise correction of flatfoot syndrome.

In addition to the positioning of the anchoring thread and to limit the impact, on the implant, of micromovements related to walking, the retaining elements present on the surface of the head combat any rotation of the implant about its axis of insertion. These retaining elements for blocking in rotation also cooperate with the position of the anchoring thread in order to prevent any backwards movement of the implant after its implantation.

Finally, it can be noted that this implant has a design that is one-piece and does not have a specificity of implementation as complicated and costly as that that an implant of the screw-expanding anchor type can have.

The depressions create spaces located inside the cone of revolution formed by the head.

These spaces created by the depressions are intended for fibrous integration and allow the trapping of the cone by the colonising soft tissue at a depth. The effects of the fibrous colonisation are thus optimised by the retaining elements for blocking the implant in rotation about its axis of insertion, according to an exemplary embodiment of the disclosure.

The capacity of the head to be inscribed inside a polygon, which can be a regular polygon, allows the optimisation of the spaces intended for fibrous integration. The colonising tissue thus allows the cone to be trapped at a depth and blocks any rotation of the cone and thus of the subtalar implant about its axis of insertion.

The recesses increase the amount of space located inside the head that is dedicated to fibrous integration. These recesses also increase the capacity of the implant to prevent any rotation about its axis of insertion.

Due to the creation of the annular cavity or cavities, the colonising soft tissue traps the head of the implant. The effect of blocking the axial migration is reinforced.

This blocking effect is even greater because the bottom of the annular cavity or cavities also allow one or more fibrous integration polygons to be inscribed inside the cone, which effectively blocks any rotation, the annual cavity or cavities having a polygonal shape.

Indeed, an increase in the quantity of stop zone is thus observed intended to cooperate with the colonising tissue.

Advantageously, the retaining elements comprise at least one edge extending lengthwise on the radially outer surface of the head in a manner substantially overlapping with or parallel to a generatrix of the radially outer surface, creating a stop zone intended to cooperate with the colonising tissue.

Due to the edge or edges, after the colonisation, by the colonising tissue, of the space surrounding the implant, the colonising tissue exercises a resistance against any possible unscrewing of the implant.

Indeed, the edges extending lengthwise on the radially outer surface of the head, in a manner substantially overlapping with or parallel to a generatrix of the radially outer surface, thus create stop zones.

These stop zones are thus specifically oriented in such a way as to combat any rotation of the implant about its axis of insertion.

Thus, the edges of the retaining elements have an orientation such that these edges do not form a screw pitch of an anchoring thread. Thus, the edges of the retaining elements, rather than causing an unscrewing of the implant, combat an effect of unscrewing of the implant, including in the presence of the anchoring thread on the surface of the rod.

In other words, the edges create, at least on one side of said edges, a surface forming a stop zone against which the colonising tissue comes into contact and prevents the rotation, in one direction, of the implant about its axis of insertion.

Advantageously, the retaining elements comprise a plurality of edges angularly offset with respect to one another.

A plurality of edges allows the effect of retaining rotation of the implant about its axis of insertion to be amplified.

The depressions can be more or less pronounced.

According to a first approach, the depressions can have a radius of curvature greater than that of the radially outer surface of the cone of revolution.

According to a second approach, the depressions can correspond to a flat section. This second approach of course provides better performance than the first.

According to a third approach, the depressions form concavities on the radially outer surface of the cone of revolution. This third approach also provides better performance than the first approach.

The concavities allow the space dedicated to fibrous integration located inside the theoretical shape of the cone of revolution to be increased.

According to an exemplary solution, each depression is defined by two edges.

The depressions thus contribute to the formation of these edges. Indeed, the borders of the depressions thus form a plane, the intersection of which with the surface of the cone form the edges.

The depressions thus extend over the entire length of the edges.

That is to say, the depressions also extend lengthwise on the radially outer surface of the head, in a manner substantially overlapping with or parallel to a generatrix of the radially outer surface.

Thus, the presence of a significant volume dedicated to fibrous integration is coupled with the creation of the stop zones by the edges. Indeed, a significant surface area of the head of the implant forms a stop zone, and this stop zone is thus facing a significant volume dedicated to fibrous integration, thus allowing the creation of a significant resistance for combatting a rotation of the implant about its axis of insertion.

In an exemplary embodiment, the head has, on its radially outer surface, continuous smooth portions between each end of the head, the continuous smooth portions being regularly distributed around the head.

In this case, the depressions are located between two continuous smooth portions.

These continuous smooth portions allow for the homogenous and progressive penetration of the head during the implantation and limit irritations and osseous erosion. These continuous smooth portions form a continuity of the cone of revolution and thus provide a smooth surface preserved between the edges that surround a depression.

In an exemplary embodiment, the retaining elements have 3 to 10 depressions, such as 6 depressions, in a transverse cross-section perpendicular to the axis of insertion.

Advantageously, in a transverse cross-section perpendicular to the axis of insertion, the corners of the polygon are formed near the edges.

In an exemplary embodiment, the polygon is regular.

According to an exemplary embodiment, each depression has a plurality of recesses.

As explained above, these recesses increase the quantity of space located inside the head that is dedicated to fibrous integration. These recesses also increase the capacity of the implant to avoid any rotation about its axis of insertion.

According to an advantageous embodiment, the implant comprises a succession of annular cavities located along the axis of insertion inside the head, the recesses located at the same height along the axis of insertion communicating with each other inside the head in order to create one of the annular cavities.

This embodiment allows the anchoring of the implant to be maximised via the formation of a plurality of fibrous integration polygons inside the cone (the colonising tissue inside each of the annular cavities) that communicate with the outside of the implant, while preserving in a greater manner the outer surface of the head of the implant in order to optimise its contact with the osseous structures, and while being easy to manufacture.

According to an exemplary embodiment, the depressions:
are regularly distributed over the radially outer surface of the head;
extend lengthwise in a manner substantially parallel to a generatrix of the radially outer surface of the head, over at least 70% of its length.

With depressions positioned in such a way and having a length of at least 70% of that of the head, the chances of having flat contact on the surface of the bone are increased. The implant thus has better stability once implanted.

In an exemplary embodiment, the depressions extend lengthwise over substantially the entire length of the head.

Advantageously, the implant has a central cannula for guiding on a pin, the annular cavity or cavities being independent of the central guide cannula.

Due to such a central cannula for guiding on a pin, the installation of the implant is easy.

The independence of the annular cavities with respect to the central cannula allows the anchoring of the implant to be optimised via the fibrous integration polygons and the bottoms of the annular cavities receiving the fibrous integration polygons.

In an exemplary embodiment, the implant also has an inner thread inside the cannula. This inner thread allows the insertion of a threaded rod intended to be connected to the implant in order to facilitate the removal thereof.

According to an advantageous feature:
the implant has a length $L_{total}$;
the head has a length $L_{head}$, $$\text{with } 0.5 \leq \frac{L_{head}}{L_{total}} \leq 0.8, \text{ such as with } 0.69 \leq \frac{L_{head}}{L_{total}} \leq 0.77.$$

BRIEF DESCRIPTION OF THE DRAWINGS

Other features and advantages of one or more embodiments of the disclosure will be clearer upon reading the following description of various exemplary embodiments of the disclosure, given as illustrative and non-limiting examples, and the appended drawings among which.

DETAILED DESCRIPTION OF ILLUSTRATIVE EMBODIMENTS

In reference to FIGS. 1 to 5, an aspect of the present disclosure relates to a subtalar implant 1.

Figure 1:
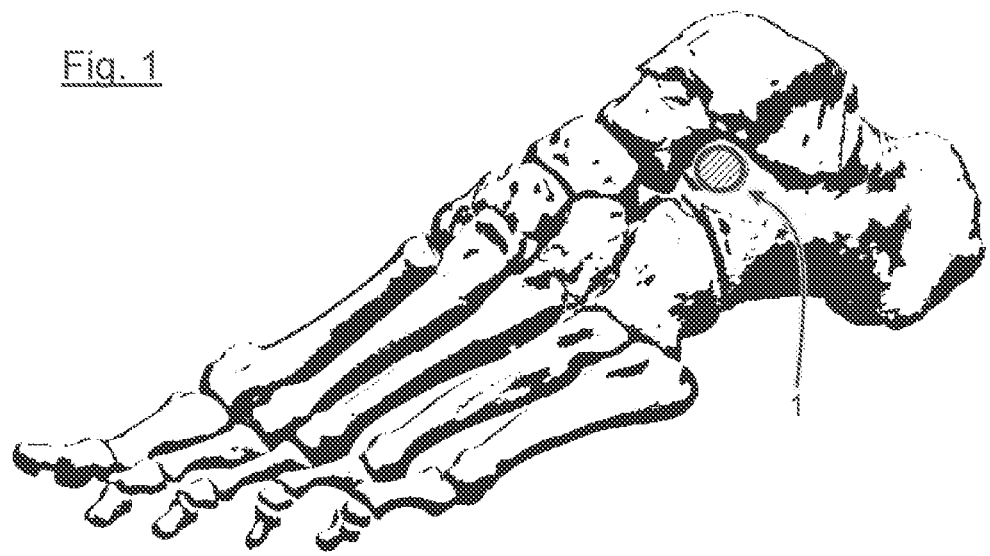
FIG. 1 is a representation of a subtalar implant according to an exemplary embodiment, inserted into the talocalcaneal joint via its lateral orifice.

In reference to FIG. 1, the subtalar implant according to an exemplary embodiment is designed for the arthroereisis of the talocalcaneal joint. The implant is intended to be inserted into the talocalcaneal joint via its lateral orifice.

In reference to FIGS. 2a, 2b, 3, 4 and 5, the subtalar implant 1 according to an exemplary embodiment has an oblong shape that extends longitudinally along an axis of insertion X of the implant into the talocalcaneal joint.

Such an implant is extra-osseous.

According to FIGS. 2a, 2b, 3, 4 and 5, the implant 1 comprises:
- a head 2;
- a rod 3.

In reference to 2a, 2b, 3, 4 and 5, the head 2 has the shape of a cone of revolution centred on the axis of insertion X. More precisely, the head 2 has the shape of a frustum.

The rod 3 has the shape of a cylinder of revolution centred on the axis of insertion.

The head flares out from the rod while being located upstream of the head along the axis of insertion X of the implant.

In other words, along the axis of insertion, the rod is located in front of the head, the head having the shape of a cone that flares out from the rod.

Figure 5:
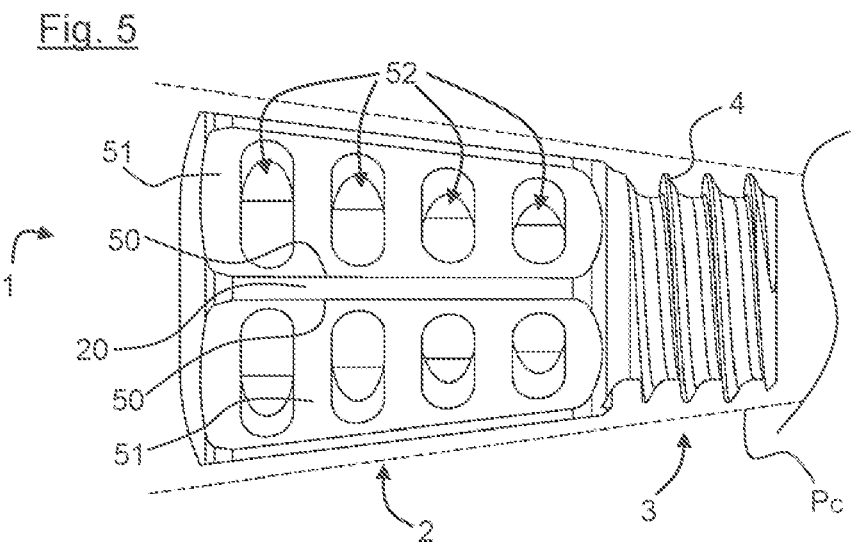
FIG. 5 is a schematic side view of the implant according to a fourth embodiment.

As illustrated by FIG. 5 and as mentioned above, the head 2 has, more precisely, the shape of a frustum from which the rod 3 extends. The rod 3 is inscribed inside the projection $P_c$ of the shape of a cone of revolution of the head, from the head and in the direction of the top of the cone.

Again according to FIGS. 2a to 5, the implant 1 comprises:
- an anchoring thread 4;
- retaining elements 5 for retaining the implant in rotation about the axis of insertion.

The anchoring thread 4 is presented by the rod on its surface. The rod, with the anchoring thread on its surface, is intended to be inserted up to the axis of rotation of the talocalcaneal joint.

The head has, on its radially outer surface, the retaining elements 5 for retaining in rotation.

The retaining elements 5 for retaining in rotation are intended to exert retention against colonising tissue.

In reference to FIGS. 2a, 4 and 6 and 7, the retaining elements 5 for retaining in rotation comprise at least one edge 50.

The edge 50 extends lengthwise over the radially outer surface 20 of the head 2 in a manner that substantially overlaps with or is parallel to a generatrix of the radially outer surface of the head. The edge 50 creates a stop zone intended to cooperate with the colonising tissue.

Indeed, an edge is formed at the intersection of two planes. The edge thus creates a stop zone (or "surface presented by the surface of the head"), which does not correspond to the shape of a cone of revolution in which said head is inscribed. This surface, after the colonisation of the soft tissue, thus forms a stop that cooperates with the colonising tissue in order to exert retention against the rotation of the implant about its axis of insertion.

The edge, by extending lengthwise on the radially outer surface of the head in a manner that substantially overlaps with or is parallel to a generatrix of the radially outer surface of the head, cannot be equated with the anchoring thread located on the rod.

Figure 7:
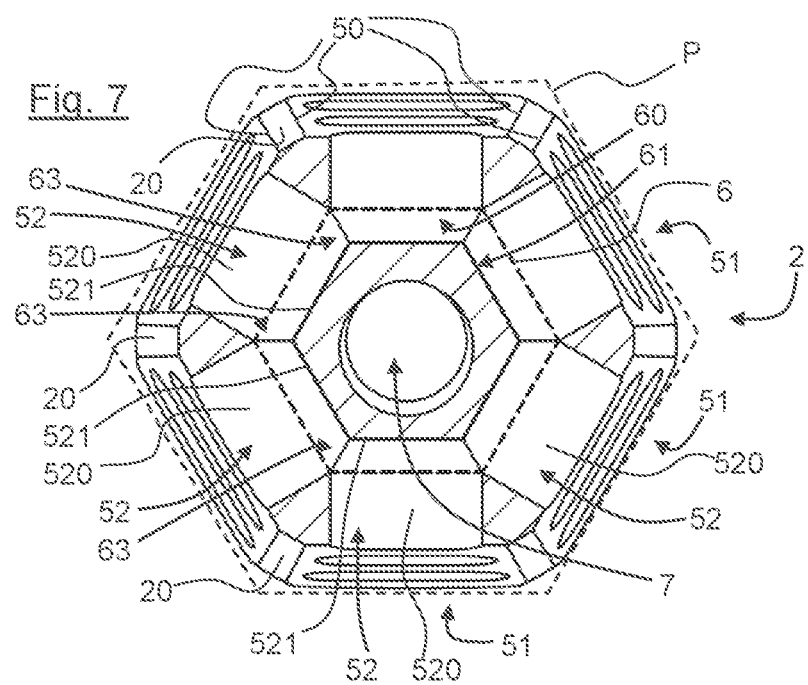
FIG. 7 is a cross-sectional view of FIG. 6.

In reference to FIG. 7, the retaining elements 5 for retaining in rotation comprise a plurality of edges 50 offset angularly with respect to one another.

The retaining elements 5 for retaining in rotation also comprise depressions 51 with respect to the shape of a cone of revolution of the head. These depressions correspond more precisely to an offset of the outer surface of the head with respect to theoretical shape of a cone of revolution in which the head is inscribed.

Figure 2A:
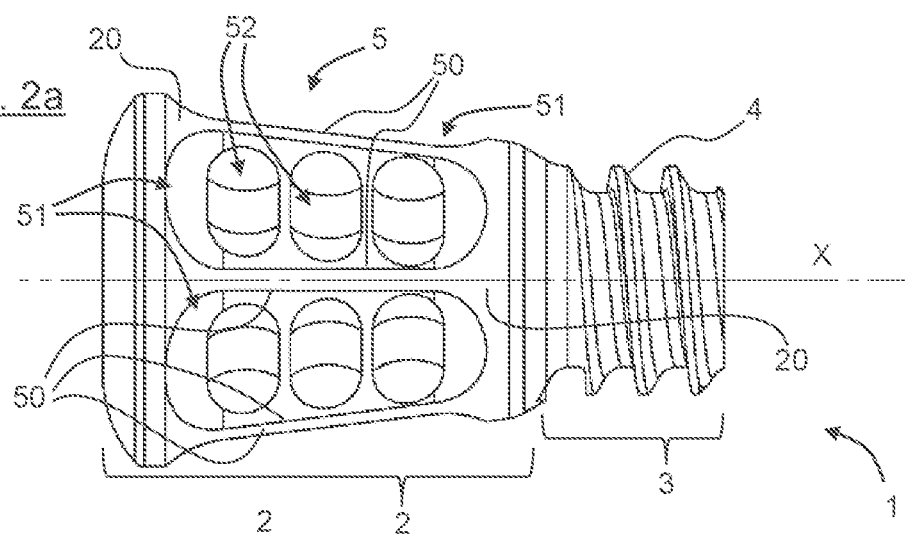
FIGS. 2a and 2b are schematic views of a first embodiment of the implant, in a lateral view and a longitudinal cross-section passing through the axis of insertion.
Figure 2B:
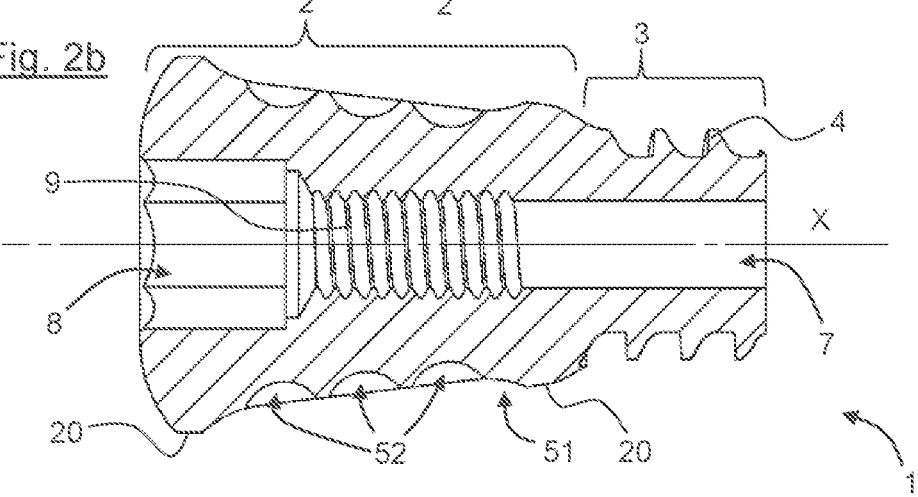

According to the embodiment illustrated by FIGS. 2a and 2b, the depressions 51 take the shape of longitudinal grooves that substantially overlap with or are parallel to a generatrix of the radially outer surface of the head.

Figure 3:
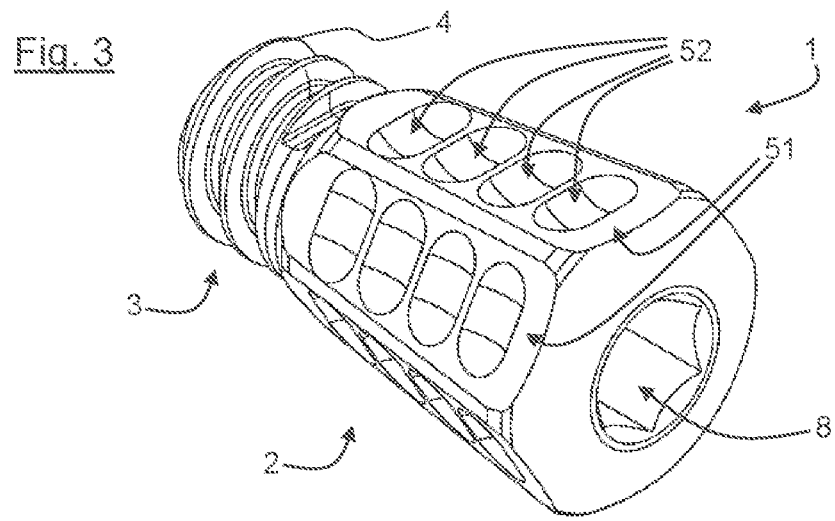
FIG. 3 is a perspective view of a second embodiment of the disclosure.

According to the embodiment illustrated by FIG. 3 and by the embodiments illustrated by FIGS. 4, 5, 6 and 7, the depressions 51 take the shape of flat sections.

Figure 6:
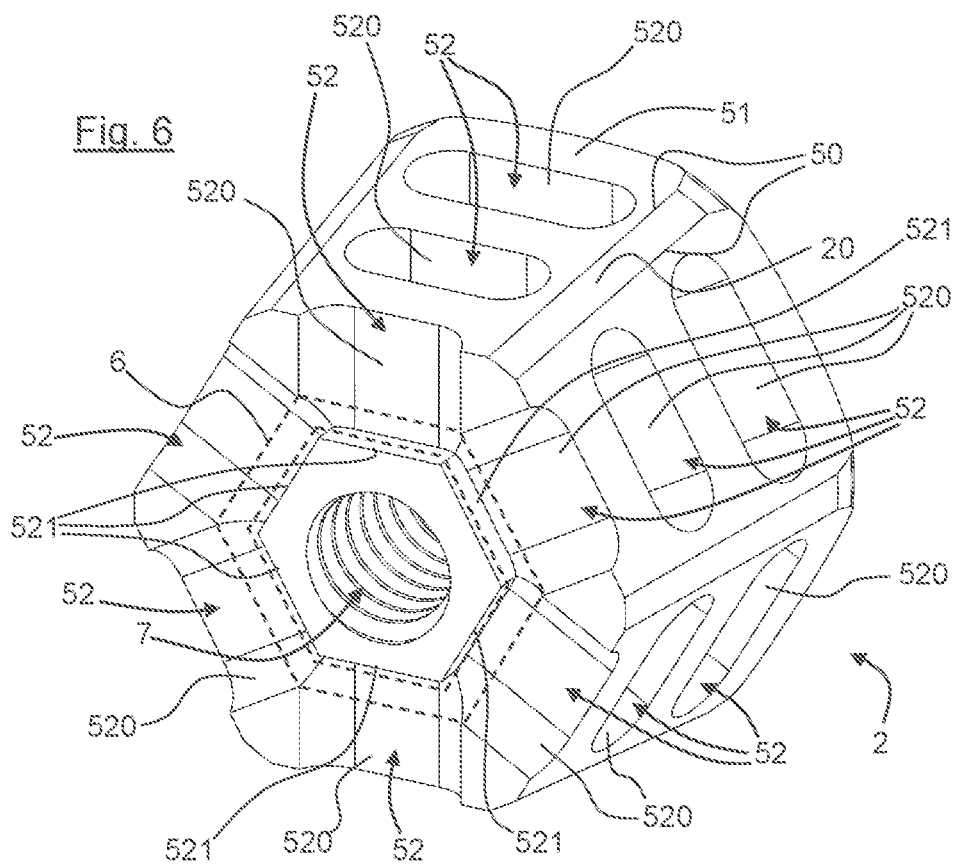
FIG. 6 is a schematic perspective view of a portion of the head of the implant of FIG. 5.

In reference to FIGS. 6 and 7, each depression 51 (taking the shape of flat sections) is defined by two edges 50.

In this case, said edges are formed during the creation of the flat sections and correspond to the intersection of the lateral edges of the flat section with the surface of the cone.

In reference to FIGS. 2a, 4, 5, 6 and 7, the head 2 has, on its radially outer surface, continuous smooth portions 20 between each end of the head. These continuous smooth portions correspond to the radially outer surface 20 of the head that is inscribed in the cone of revolution.

These continuous smooth portions are regularly distributed around the head. They thus allow a continuity of the cone of revolution to be formed.

As illustrated by these drawings, each depression is located between two continuous smooth portions.

In reference to FIG. 7, in a transverse cross-section perpendicular to the axis of insertion, the retaining elements for retaining in rotation have six depressions.

Again in the transverse cross-section perpendicular to the axis of insertion, the head is inscribed in a polygon P, the sides of which extend at the depressions and the corners of which are formed near the edges.

According to the present embodiment, the polygon P is regular.

The capacity of the head to be inscribed in a polygon allows its anchoring inside a fibrous integration polygon.

With this embodiment, the colonising soft tissue can trap the cone at a depth and block the axial rotation.

The depressions can also be put in contact with certain osseous surfaces during the implantation. A possible rotation can thus be blocked in a much more efficient manner.

In reference to FIGS. 2a to 7, the retaining elements 5 for retaining in rotation can also comprise recesses 52 located inside the depressions 51.

In reference to FIGS. 2a, 2b, 3 and 4, the recesses 52 are blind.

Figure 4:
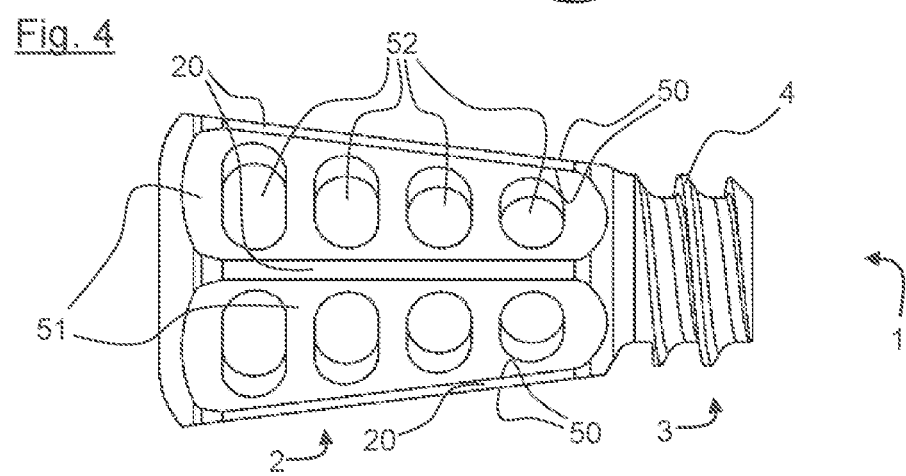
FIG. 4 is a schematic view of a third embodiment of the disclosure, in a lateral view.

In reference to the embodiment illustrated by FIGS. 4, 5 and 6, the recesses 52 take the shape of a transverse groove perpendicular or substantially perpendicular to a generatrix of the radially outer surface of the head.

According to the embodiments illustrated by FIGS. 5 to 7, the recesses 52 communicate with each other inside the head 2. The recesses thus communicate to create one or more annular cavities 6 (illustrated by FIGS. 6 and 7) that are intended to be colonised by colonising tissue.

This or these annular cavities take the shape of a polygon, or have a "polygonal shape." More precisely, the annular cavity or cavities have a hexagonal shape.

Indeed, in reference to FIGS. 6 and 7, each recess 52 is formed by a peripheral wall 520 and by a bottom 521, the peripheral wall extending from the bottom 521 to the surface of the head 2 of the implant 1. The bottom 521 of each recess is thus formed according to the depth of the recess 52. These bottoms 521 are flat.

As illustrated by these drawings, the bottoms 521, joined end to end have the shape of a polygon (or "a polygonal cross-section"), in particular the shape of a regular polygon, and even more precisely a hexagonal shape.

The annular cavities 6 are thus created due to the formation of communication passages 63 between the recesses 52 that are adjacent to each other. The communication passages 63 are in this case formed by the junction of the peripheral walls 520.

In other words and in reference to FIG. 7, the annular cavities 6 define an annular volume that has, in a transverse cross-section perpendicular to the axis of insertion, an inner perimeter 61 and an outer perimeter 60 (the inner perimeter 61 being more precisely formed by the bottom 521 of the recesses 52) that both have the shape of a polygon, in particular the shape of a regular polygon, and more precisely the shape of a hexagon.

According to the present embodiment illustrated by FIGS. 6 and 7, the recesses located at the same height along the axis of insertion communicate with each other to create an annular cavity. The annular cavity created is independent of those created by recesses located at a different height along the axis of insertion.

According to a non-illustrated embodiment, recesses directly adjacent and located at at least two different heights can create the same annular cavity.

As illustrated by FIG. 5, the implant comprises a succession of annular cavities located along the axis of insertion inside the head 2.

These annular cavities 6 contribute to the maximisation of the space intended for fibrous integration located inside the head.

In reference to FIGS. 2b, 6 and 7, the implant 1 has a central cannula 7 for guiding on a pin. As illustrated by FIGS. 6 and 7, the annular cavities 6 are independent of the central guide cannula.

According to FIGS. 2b and 3, the head 2 of the implant 1 also comprises a drive element 8. The drive element 8 of the implant is in the shape of a rear cavity having six sides.

In reference to FIG. 2b, the drive element 8 communicates with the central guide cannula 7. This central guide cannula 7 has an inner thread 9 inside the cannula. This inner thread allows the coupling of the implant with a threaded rod intended to allow the removal of the implant to be facilitated.

The implant according to an exemplary embodiment can be made from titanium, from an alloy of titanium, from poly ethylene, from PEEK (polyetheretherketone), or from a resorbable biopolymer (PLLA ((L)-lactic acid), PLA (polylactic acid), PGA (polyglycolic acid) or a hybrid).

As illustrated by the drawings, the implant according to an exemplary embodiment is in one piece. That is to say, the implant is made from a single part.

Such an implant according to an exemplary embodiment can be manufactured via turning/machining. It thus has a lower manufacturing cost than modes of manufacturing via addition of material.

For information:
the diameter at the rear of the head can be between from 5 to 20 mm;
the total length of the implant is between from 10 to 20 mm;
the length of the head is between from 5 to 16 mm.

In an exemplary embodiment, the total length of the implant is between 13.5 to 18 mm and the length of the head is between 6.9 to 15.4 mm.

An exemplary embodiment of the present application overcomes the disadvantages of the prior art.

An exemplary embodiment proposes a subtalar implant, for arthroereisis of the talocalcaneal joint, that is extraosseous and that does not tend at all or at the very most only slightly tends to move backwards once it has been inserted and the colonisation of the fibrous tissue has taken place, under the effect of micromovements related to walking.

An exemplary embodiment proposes such a subtalar implant that does not tend to irritate the surrounding tissue and osseous structures.

An exemplary embodiment proposes such a subtalar implant that does not have a complicated and costly implementation.

Although the present disclosure has been described with reference to one or more examples, workers skilled in the art will recognize that changes may be made in form and detail without departing from the scope of the disclosure and/or the appended claims.

The invention claimed is:

1. A subtalar implant for arthroereisis of the talocalcaneal joint, the implant configured to be inserted into the talocalcaneal joint via its lateral orifice, the implant being one-piece and comprising:
   an oblong shape that extends longitudinally along an axis of insertion of the implant;
   a head having a shape of a cone of revolution centred on the axis of insertion;
   an anchoring thread;
   a rod having a shape of a cylinder of revolution centred on the axis of insertion, the rod having, on its surface, the anchoring thread and being arranged to be inserted up to the axis of rotation of the talocalcaneal joint, the head flaring out from the rod and being located upstream of the head along the axis of insertion of the implant, the head having, on its radially outer surface, retaining elements for retaining the implant in rotation about the axis of insertion, the retaining elements being arranged to exert retention against a colonising tissue, wherein the retaining elements comprise:
      a plurality of depressions with respect to the shape of the cone of revolution of the head;
      at least one recess located inside each of the depressions, the at least one recess communicating with the at least one recess of at least one other of the plurality of depressions inside the head in order to create at least one annular cavity to be colonised by colonising tissue, each of the plurality of recesses having a bottom, which is flat,
   wherein, in a transverse cross-section perpendicular to the axis of insertion:
      the head is inscribed inside a first polygon, wherein sides of which extend at the depressions;
      for each of the at least one annular cavity, the bottoms of the recesses of that annular cavity joined end to end have a shape of a second polygon such that the annular cavity has a polygonal shape, suitable for allowing inscription of a fibrous integration polygon inside the head.

2. The implant according to claim 1, wherein the retaining elements comprise at least one edge extending lengthwise on the radially outer surface of the head in a manner substantially overlapping with or parallel to a generatrix of the radially outer surface, creating a stop zone to cooperate with the colonising tissue.

3. The implant according to claim 2, wherein the retaining elements comprise a plurality of edges angularly offset with respect to one another.

4. The implant according to claim 3, wherein each depression is defined by two edges.

5. The implant according to claim 4, wherein in a transverse cross-section perpendicular to the axis of insertion, the corners of the first polygon are formed near the edges.

6. The implant according to claim 1, wherein the first polygon is regular.

7. The implant according to claim 1, wherein each depression has a plurality of recesses.

8. The implant according to claim 7, wherein the implant further comprises a succession of annular cavities located along the axis of insertion inside the head, the recesses located at a same height along the axis of insertion communicating with each other inside the head in order to create one of the at least one annular cavity.

9. The implant according to claim 1, wherein the depressions:

are regularly distributed over the radially outer surface of the head;

extend lengthwise in a manner substantially parallel to a generatrix of the radially outer surface of the head, over at least 70% of a length of the head.

10. The implant according to claim 9, wherein the depressions extend lengthwise over substantially the entire length of the head.

11. The implant according to claim 10, wherein the implant has a central cannula for guiding on a pin, the at least one annular cavity being independent of the central guide cannula.

12. The implant according to claim 1, wherein the annular cavity defines an annular volume that has, in the transverse cross-section perpendicular to the axis of insertion, an inner perimeter and an outer perimeter that both have a polygonal shape, the inner perimeter being formed by the bottoms of the recesses.

* * * * *